United States Patent [19]
Singh et al.

[11] Patent Number: 6,004,966
[45] Date of Patent: Dec. 21, 1999

[54] USE OF XANTHINE OXIDASE INHIBITORS AS ANTI-ISCHAEMIC AGENTS

[75] Inventors: Surinder Singh, West Croydon; Anthony Edward Lewis, London, both of United Kingdom

[73] Assignee: BTG International Limited, London, United Kingdom

[21] Appl. No.: 08/871,883

[22] Filed: Jun. 9, 1997

Related U.S. Application Data

[63] Continuation of application No. PCT/GB95/02980, Dec. 8, 1995.

[30] Foreign Application Priority Data

Dec. 9, 1994 [GB] United Kingdom .................. 9424842

[51] Int. Cl.[6] .......................... A01N 43/54; A01N 43/90; C07D 475/00; C07D 473/00
[52] U.S. Cl. .......................... 514/258; 514/261; 514/262; 514/263; 544/257; 544/264; 544/265; 544/266; 544/267
[58] Field of Search .................................... 544/350, 257, 544/264, 265, 266, 267; 514/249, 258, 261, 262, 663

[56] References Cited

U.S. PATENT DOCUMENTS 4,757,078  7/1988  Misra ...................................... 514/309

OTHER PUBLICATIONS

Lam et al., "Photochemistry of Some Pteridine N–Oxides,"*J. Org. Chem.,* vol. 43, No. 1, pp. 167–168, New York, NY (1978).
Tserng et al., Electron impact–induced fragmentation of 3–hydroxy quinazoline–2,4(1H,3H) dione, J. Heterocycl. Chem. 12 (1), 79–83, 1975.
Murahashi et al., "Tunstate–catalyzed Oxidation . . . ", J. Org. Chem. 55 (1990) 1744–1749.
Myles et al., "Purine N–Oxides", J. Bio. Chem., 244:15 (1969) 4072–4076.
Murahashi et al., "Tungstate–catalyzed Oxidation . . . ", J. Chem. Soc. Chem. Commun. (1987) 1470–1473.
Christie et al., "Cyclisation to Schiff . . . ", J. Chem. Soc. Perkin Trans. 1 (1985) 2779–2783.
Eckstein et al., "A Facile Rearrangement . . . ", Heterocycles 20:10 (1983) 1898–1901.
Dubby et al., "Influence of Some Ionic . . . ", J. Indian Chem. Soc. LIX (1982) 706–709.
Anderson et al., "Increased Incidence of Mammary . . . ", J. Natl. Cancer Inst. 61:6 (1978) 1410–1415.
Lam et al., "Photochemistry of Some . . . ", J. Org. Chem. 43:1 (1978) 167–169.
Parham et al., "Purine N–Oxides . . . ", J. Org. Chem. 36:18 (1971) 2638–2647.
Lion et al., "Nouveaux Decontaminants . . . ", Bull. Soc. Chim. Belg. 100:8 (1991) 616–621.
Parham et al., "Purine N–Oxides . . . ", Liss 32 (1967) 1150–1155.
Fahmy et al., "Novel Synthesis of Pyridopyrimidine Diones", Heterocycles 24:8 (1986) 2200–2213.
Lee et al., "Chemical Reactivities and Oncogenicites . . . " Chem.–Biol. Interactions 25 (1979) 369–373.
DE,A, 23 56 690 (Kohjin Co., Ltd.) May 30, 1974.

(List continued on next page.)

*Primary Examiner*—Jose' G. Dees
*Assistant Examiner*—Alton Pryor
*Attorney, Agent, or Firm*—Nixon & Vanderhye

[57] ABSTRACT

The use of a compound of formula I

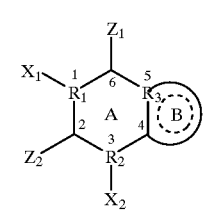

in which $R_1$ and $R_2$ are N, $X_1$ and $X_2$ which may be the same or different are hydrogen, hydroxy, or an optionally substituted alkyl, and $Z_1$ and $Z_2$ which may be the same or different are hydrogen, hydroxy, keto (=O), or one of $Z_1$ and $X_1$ and $Z_2$ and $X_2$ form a second bond of a double bond at the 1,6 or 2,3 positions with the proviso that at least one of the groupings $R_1Z_1X_1R_2Z_2X_2$ and $R_1X_1Z_2$ form a hydroxamate moiety (—N(OH)C(=O)—) in which $R_1$ and $R_2$ is N, $Z_1$ and/or $Z_2$ is =O and $X_1$ and/or $X_2$ is OH or $R_1$ is N, $Z_2$ is =O and $X_1$ is OH and B is a 5 or 6 membered ring of formula II or III

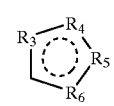

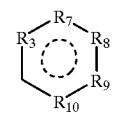

in which $R_4$, $R_5$, $R_6$, $R_7$, $R_8$, $R_9$, and $R_{10}$ which may be the same or different are CH or N with the proviso that ring B cannot contain more than 3 ring members which are nitrogen and the ring B may optionally be substituted with a physiologically acceptable organic or inorganic acid, for the manufacture of a medicament for use as an anti-ischaemic agent.

20 Claims, 4 Drawing Sheets

OTHER PUBLICATIONS

J. Clark et al, "Heterocyclic studies. Part IV. The action of hydroxylamine on 4–hydroxypteridine and its methyl derivatives", J. Chem. Soc. (c), vol. 8, 1968, pp. 919–922.

J.A. Montgomery et al. "1–Glycosyl derivatives of 5–aminoimidazole–4–carboxamide", J. Med. Chem., vol. 15, No. 12, 1972.

G.R. Revankar "Synthesis and antiviral activity of certain 5'–monophosphates of 9–D–arabinofuranosyladenine and 9–D–arabinofuranosylhypoxanthine", J. Med. Chem. vol. 18, No. 7, 1975 pp. 721–726.

M.N. Teller et al. "Comparison of the oncogenicites of four structrally isomeric N–hydroxyxanthines", Cancer Res., vol. 38, No. 7, 1978, pp. 2038–2042.

L. Bauer et al. "Pyrazolo–N–hydroxyuracils from the modified Lossen rearrangement of vicinal pyrazoledicarbohydroxamates", J. Heterocycl. Chem., vol. 4 No. 3, 1967, pp. 325–334.

M. Borbil et al., "Molecular orbital calculations for purine–N–oxides", Rev. Roum. Biochim., vol. 15, No. 1, 1978, pp. 3–8.

AN–93–338929, Database WPI Week 9343, Derwent Publications, Ltd. London, GB.

EP, A, 0 237 348 (The Wellcome Foundation Ltd.) Sep. 16, 1987—see page 2.

USE OF XANTHINE OXIDASE INHIBITORS AS ANTI-ISCHAEMIC AGENTS

This application is a cont. of PCT application Ser. No. PCT/GB95/02980 filed Dec. 8, 1995.

BACKGROUND TO THE INVENTION

1. Field of the Invention

This invention relates to pharmaceutical compounds and to compositions containing them, being primarily concerned with substances of use as anti-ischaemic agents.

2. Description of the Prior Art

Free radicals are reactive substances produced constantly in the body during respiration, tissue turnover, tissue repair and in combatting infections. Under normal conditions, the antioxidant defence mechanisms operational in the body are able to minimise biological damage. However, there are situations, e.g. in certain disease processes, when free radical production overwhelms the natural defence mechanisms.

A substantial amount of evidence has been accumulated which suggests that oxygen free radicals mediate ischaemia-reperfusion injury in a variety of tissues, including the heart, lung, kidney, gastrointestinal tract, brain and inflammatory joint disease such as rheumatoid arthritis (Korthius and Granger, 1986, in 'Physiology of Oxygen Radicals' Eds. Taylor, Matalos and Ward; Allen et al., 1989, Lancet ii, 282–283). Both direct and spin trapping EPR techniques have demonstrated that a burst of oxygen free radical production occurs after reperfusion of ischaemic tissue (Blasig et al., 1986 Stud. Biophys. 116, 35–42; Arroyo et al., 1987 FEBS Lett. 221 101–104; Zweier et al., 1987 PNAS USA 84, 1404–1407; Allen et al., 1989, Lancet ii, 282–283). Ischaemia-reperfusion injury is thought to involve a multi-component process with a burst of free radical production occurring following reperfusion and a second event, possibly inflammatory damage, occurring later. Based on the protective effects of intravascularly administered selective enzyme inhibitors and radical scavenging agents/enzymes, it is widely believed that xanthine oxidase associated with endothelial cells is probably the main source for the production of oxygen radicals responsible for inducing tissue damage during the reperfusion phase.

Treatment of ischaemia/reperfusion induced injury requires the development of compounds which suppress the harmful effects of oxygen radicals during both the reperfusion and inflammatory phases. An obvious approach would be the administration of agents that selectively block currently known pathways of radical generation and the release of inflammatory mediators. For example, peroxynitrite, formed by the reaction of nitric oxide and superoxide is thought to be one of the species responsible for bringing about the toxicity of the oxygen free radicals but inhibition of nitric oxide production may be deleterious because of its physiological role in regulating thrombogenicity and vasodilation. A more suitable target would be the inhibition of superoxide production. The above is a particularly attractive strategy, due to the possibility of selectively inhibiting xanthine oxidase, the enzyme involved in the first (reperfusion) stage of ischaemic injury.

Due to the multifactorial nature of ischaemia induced injury, in addition to xanthine oxidase inhibitory activity, compounds with potent anti-oxidant activity are required to minimise free radical mediated damage to biological molecules during both the reperfusion and inflammatory phases in disease states wherein these symptoms manifest themselves. Finally compounds which bind redox active metals such as iron with high affinity such that the metal complex is not able to take part in redox cycling reactions will provide additional benefit.

It has been a problem to find compounds which fulfil some or all these requirements.

SUMMARY OF THE INVENTION

It has surprisingly been found that compounds which are structurally analogous to natural substrates of the enzyme xanthine oxidase or which have inhibitory properties towards the enzyme xanthine oxidase, thus in both cases acting as xanthine oxidase inhibitors, fulfil some or all of the above requirements.

Accordingly, the invention provides the use of a compound of formula I

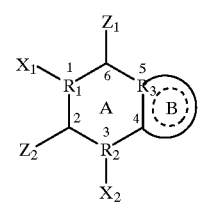

in which $R_1$, $R_2$ and $R_3$ which may be the same or different are N or CH, $X_1$ and $X_2$ which may be the same or different are hydrogen, hydroxy, or an optionally substituted alkyl, alkenyl, alkynyl, cycloalkyl, aryl or heterocyclyl group and $Z_1$ and $Z_2$ which may be the same or different are hydrogen, hydroxy, keto (=O), or an optionally substituted alkyl, alkenyl, alkynyl, cycloalkyl, aryl or heterocyclyl group or one of $Z_1$ and $X_1$ and $Z_2$ and $X_2$ form the second bond of a double bond at the 1,6 or 2,3 positions, with the proviso that at least one of the groupings $R_1Z_1X_1$, $R_2Z_2X_2$ and $R_1X_1Z_2$ form a hydroxamate moiety (—N(OH)C(=O)—) in which $R_1$ and/or $R_2$ is N, $Z_1$ and/or $Z_2$ is =O and $X_1$ and/or $X_2$ is OH or $R_1$ is N, $Z_2$ is =O and $X_1$ is OH and B is a 5 or 6 membered ring of formula II or III

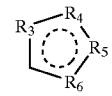

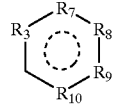

in which $R_4$, $R_5$, $R_6$, $R_7$, $R_8$, $R_9$ and $R_{10}$ which may be the same or different are CH or N with the proviso that ring B cannot contain more than 3 ring members which are nitrogen and the ring B may optionally be substituted by one or more of hydroxy, keto (=O) and an optionally substituted alkyl, alkenyl, alkynyl, cycloalkyl, aryl or heterocyclyl group, or a salt thereof formed with a physiologically acceptable organic or inorganic acid, for the manufacture of a medicament for use as an anti-ischaemic agent.

It will be appreciated that when $Z_1$ is =O and $X_1$ is H or when $Z_2$ is =O and $X_2$ is H then the grouping —C(=O)—CH$_2$— or —C(=O)—NH— can exist in the tautomeric form —C(OH)=CH— or C(OH)=N— respectively.

DESCRIPTION OF THE PREFERRED EMBODIMENTS

In the above general formula, whenever the compounds of the invention contain an alkyl, alkenyl or alkynyl substituent group, this may be linear or branched and may contain up to 10 and more preferably up to 4 carbon atoms. A cycloalkyl (referring to a cyclic hydrocarbyl group) group may contain from 3 to 8, preferably 3 to 6, carbon atoms. An aryl group refers to any aromatic hydrocarbon group, especially a phenyl, benzyl or naphthyl group. A heterocyclyl group may be any saturated or unsaturated cyclic group containing at least one heteroatom, 5- and 6-membered rings being especially preferred.

When any of the foregoing substituents are designated as being optionally substituted, the substituent groups which are optionally present include, for example, halogen atoms, hydroxyl, alkyl, alkoxy, amino, alkylamino, dialkylamino, formyl, alkoxycarbonyl, carboxyl, alkanoyl, carbamoyl, alkylamido, phenyl, cyano, nitro and phenoxy groups. When any of the foregoing substituents represents or contains an alkyl substituent group, this may be linear or branched and may contain up to 4 carbon atoms.

Regarding ring A, there may be two hydroxamate moieties at positions 1-6 or 2-3 of the ring present or more preferably only one hydroxamate moiety at positions 1-6,2-3 or 1-2 of the ring present. This is preferably at positions 1-6 or 2-3 of the ring. There may be one, two or three nitrogen atoms in ring A but preferably, there are two nitrogen atoms present in ring A, and one necessarily being part of the hydroxamate moiety. It is also possible that ring A contains only one nitrogen atom, that necessarily being part of the hydroxamate.

$X_1$ is preferably H when $R_1$ is N, and the hydroxamate moiety is present at positions 2-3 of ring A. If $R_1$ is C, then $X_1$ may be any of the substituents defined above but is most preferably H.

When the hydroxamate moiety of ring A is at position 1-6 of the ring and $R_2$ is N, $X_2$ is preferably H. When $R_2$ is C, $X_2$ is any of the above substituents but preferably H.

In all cases, ring A is preferably diketo, that is $Z_1$ and $Z_2$ are both a keto group (=O).

It is preferable that the compounds of the present invention differ from their 'natural' counterparts, i.e. they are not known xanthine oxidase inhibitors or substrates but analogues thereof.

Ring A as defined above also encompasses any tautomeric forms which would be apparent to a person skilled in the art.

Regarding ring B, when ring B is a 5 membered ring, the 5-membered ring is preferably pyrrole (containing 1N), imidazole (containing 2N), pyrazole (containing 2N) and triazole (containing 3N). When ring B is a 6-membered ring, the 6 membered ring is preferably benzene, pyridine (containing 1N) or pyrazine (containing 2N).

Both ring B of formulas II and III may optionally be substituted in one or more positions with substituents as defined above. If substituted, preferred substituents are alkyl, hydroxyl or benzyl but more preferably, ring B is not substituted.

Particularly preferred compounds of the present invention are analogues of the xanthine oxidase inhibitors allopurinol and oxypurinol and analogues of the xanthine oxidase substrates hypoxanthine and xanthine in which the hydrogen atom attached to the ring nitrogen at the 1 position in Formula I is replated by a hydroxyl group.

Particularly preferred compounds however are those wherein B is a 6 membered pyrazine group. In these compounds preferably, ring A is diketo. A specifically preferred compound is, hereinafter referred to as SL301 is 2,6-dioxo-1-hydroxypyrazino-[2,3-d]-pteridine (in Formula 1, $X_1$ is OH, $X_2$ is H, $R_1$ and $R_2$ are N, $R_3$ is CH, $Z_1$ and $Z_2$ are keto, ring B is a pyrazine ring wherein $R_7$ and $R_{10}$ are N, $R_8$ and $R_9$ are CH). The structural formula of SL301 is shown below.

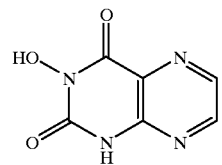

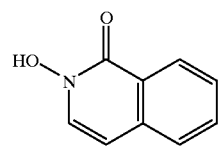

has been described in EPO 240 859 B (Abbott Laboratories) as a compound which inhibits lipoxygenase and as such is useful as an anti-inflammatory agent. U.S. Pat. No. 4,757,078 (Misra) discloses the same compound as an inhibitor of leukotriene production. Again, its potential use as an anti-allergy agent is discussed. There is no disclosure of the use of this compound as an anti-ischaemic agent.

German patent number 2,356,690 discloses compounds of the formula

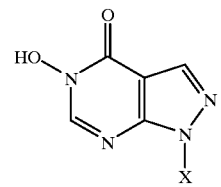

wherein X is H, aryl, $C_{1-4}$ alkyl, or $C_{1-4}$ hydroxyalkyl for treatment of gout. Again, there is no disclosure of the use of these compounds as anti-ischaemic agents.

Clark et al. J. Chem. Soc. 1968, 313, 919–922. discloses compounds having the following formula

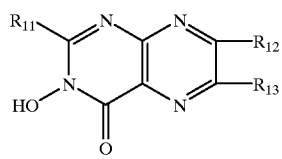

in which $R_{11}=R_{12}=R_{13}=H$
$R_{11}=CH_3, R_{12}=R_{13}=H$
$R_{12}=CH_3, R_{11}=R_{13}=H$
$R_{13}=CH_3, R_{11}=R_{12}=H$
$R_{11}=H, R_{12}=R_{13}=CH_3$
$R_{12}=H, R_{11}=R_{13}=CH_3$ No therapeutic use of these compounds is suggested.

Montgomery et al. J. Med. Chem. 1972, 15, 1334–1336 discloses compounds which have an anticancer effect. The compounds are prepared from intermediates which include

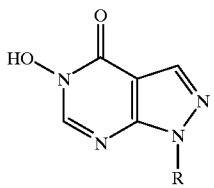

wherein R=cyclopentyl, β-D-ribofuranosyl, β-D-arabinofuranosyl, or 2-deoxy-β-D-ribofuranosyl.

Revankar et al. J. Med. Chem., 18, 1975, 721–726 discloses compounds as having anti-viral properties. The following is an intermediate in their preparation but is not disclosed as having any anti-viral activity itself.

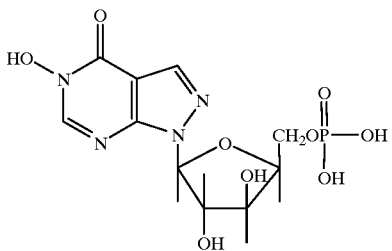

Teller et al., Cancer Research 38, 1978, 2038–2042 describes oncogenicity of N-hydroxyxanthines. Compounds included in the discussion are 1-hydroxyxanthine and 3-hydroxyxanthine.

Borbil et al. Rev. Roum. Biochim., 1978 15, 3–8 discloses cystostatic compounds including the following:

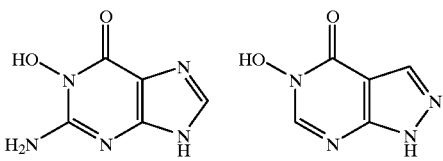

Bauer et al., J. Heterocyclyl Chemistry 1967, 4, 325–334 discloses compounds including the following:

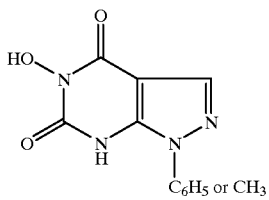

These compounds are described as being potential anti-metabolites.

It will thus be appreciated that certain of the compounds of formula I are novel. Thus the invention extends these compounds per se, processes for their preparation and their use in therapy.

Thus according to a further aspect of the invention there is provided a compound of formula I

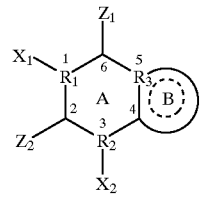

in which $R_1$, $R_2$, and $R_3$ which maybe the same or different are N or CH, $X_1$ and $X_2$ which may be the same or different are hydrogen, hydroxy, or an optionally substituted alkyl, alkenyl, alkynyl, cycloalkyl, aryl or heterocyclyl group and $Z_1$ and $Z_2$ which may be the same or different are hydrogen, hydroxy keto (=O), or an optionally substituted alkyl, alkenyl, alkyny, cycloalkyl, aryl or heterocyclyl group or one of $Z_1$ and $X_1$ and $Z_2$ and $X_2$ form the second bond of a double bond at the 1,6 or 2,3 positions with the proviso that at least one of the groupings $R_1Z_1X_1R_2Z_2X_2$ and $R_1 X_1 Z_2$ form a hydroxamate moiety (—N(OH)C(=O)—) in which $R_1$ and/or $R_2$ is N, $Z_1$ and/or $Z_2$ is =O and $X_1$ and/or $X_2$ is OH or $R_1$ is $N_1Z_2$ is =O and $X_1$ is OH and B is a 5 or 6 membered ring of formula II or III

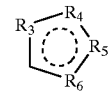

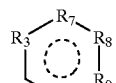

in which $R_4$, $R_5$, $R_6$, $R_7$, $R_8$, $R_9$ and $R_{10}$ which may be the same or different are CH or N with the proviso that ring B cannot contain more than 3 ring members which are nitrogen and the ring B may optionally be substituted by one or more of hydroxy, keto (=O), or an optionally substituted alkyl, alkenyl, alkynyl, cycloalkyl, aryl or heterocyclyl group with the proviso that the compound is not

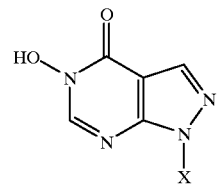

wherein X is hydrogen, aryl, $C_{1-4}$ alkyl, or $C_{1-4}$ hydroxyalkyl or

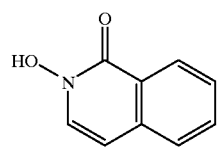

-continued

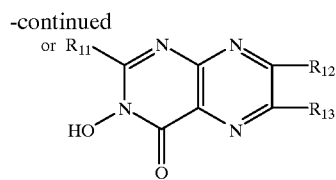

wherein
$R_{11}=R_{12}=R_{13}=H$
$R_{11}=CH_3, R_{12}=R_{13}=H$
$R_{12}=CH_3, R_{11}=R_{13}=H$
$R_{13}=CH_3, R_{11}=R_{12}=H$
$R_{11}=H, R_{12}=R_{13}=CH_3$
$R_{12}=H, R_{11}=R_{13}=CH_3$

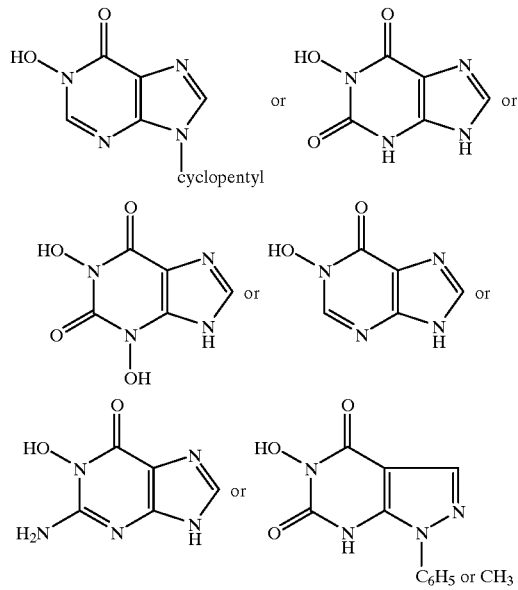

or any compound of Formula I wherein ring B is substituted by a natural or unnatural sugar molecule or a salt thereof formed with a physiologically acceptable organic or inorganic acid.

The definitions regarding rings A and B have been given hereinbefore. The following are particularly preferred novel compounds of the invention. This also extends to their use in therapy and their formulation into a pharmaceutical composition.

Regarding ring A, there may be two hydroxamate moieties at positions 1, 6 or 2, 3 of the ring present or more preferably only one hydroxarnate moiety at positions 1, 6, 2, 3 or 1, 2 of the ring present. This is preferably at positions 1, 6 or 2, 3 of the ring. There may be one, two or three nitrogen atoms in ring A but preferably, there are two nitrogen atoms present in ring A, and one necessarily being part of the hydroxamate moiety. It is also possible that ring A contains only one nitrogen atom, that necessarily being part of the hydroxamate.

$X_1$ is preferably H when $R_1$ is N, and the hydroxamate moiety is present at positions 2, 3 of ring A. If $R_1$ is C, then $X_1$ may be any of the substituents defined above but is most preferably H.

When the hydroxamate moiety of ring A is at position 1,6 of the ring and $R_2$ is N $X_2$ is preferably H. When $R_2$ is C, $X_2$ is any of the above substituents but preferably H.

In all cases, ring A is preferably diketo, that is $Z_1$ and $Z_2$ are both a keto group (=O).

Ring A as defined above also encompasses any tautomeric forms which would be apparent to a person skilled in the art.

Regarding ring B, when ring B is a 5-membered ring, the 5-membered ring is preferably pyrrole (containing 1N), imidazole (containing 2N), pyrazole (containing 2N) and triazole (containing 3N). When ring B is a 6-membered ring, the 6-membered ring is preferably benzene, pyridine (containing 1N) or pyrazine (containing 2N).

Both ring B of formulas II and III may optionally be substituted in one or more positions with substituents as defined above. If substituted, preferred substituents are alkyl, hydroxyl or benzyl but more preferably, ring B is not substituted.

Particularly preferred compounds of the present invention are analogues of the xanthine oxidase inhibitors allopurinol and oxypurinol and analogues of the xanthine oxidase substrates hypoxanthine and xanthine in which the hydrogen atom attached to the ring nitrogen at the 1 position in Formula I is replated by a hydroxyl group.

Particularly preferred compounds however are those wherein B is a 6-membered pyrazine group. In these compounds preferably, A is diketo. A specifically preferred compound is, SL301, 1 2,6-dioxo-1-hydroxypyrazino-[2,3-d]-pteridine (in Formula I, $X_1$ is OH, $X_2$ is H, $R_1$ and $R_2$ are N, $R_3$ is CH, $Z_1$ and $Z_2$ are keto, ring B is a pyrazine ring wherein $R_7$ and $R_{10}$ are N, $R_8$ and $R_9$ are CH).

Several methods are available for the preparation of the compounds of formula I. For example, hydroxamate-containing analogues of known xanthine oxidase substrates or inhibitors such as hypoxanthine, xanthine, (substrates), allopurinol, oxypurinol (inhibitors) can be prepared by replacing the hydrogen atom attached to a ring nitrogen at the 1 position with a hydroxyl group.

Other methods of preparing the compounds of the invention will be apparent to a person skilled in the art using processes known for the preparation of chemically related compounds. Accordingly, such processes form a further feature of this invention.

According to a further aspect of the invention there is provided a compound of formula I

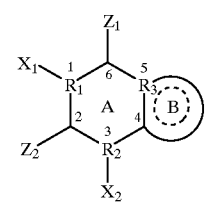

in which $R_1$, $R_2$ and $R_3$ which may be the same or different are N or CH, $X_1$ and $X_2$ which may be the same or different are hydrogen, hydroxy, or an optionally substituted alkyl, alkenyl, alkynyl, cycloalkyl, aryl or heterocyclyl group and $Z_1$ and $Z_2$ which may be the same or different are hydrogen, hydroxy, keto (=O), or an optionally substituted alkyl, alkenyl, alkynyl, cycloalkyl, aryl or heterocyclyl group or one of $Z_1$ and $X_1$ and $Z_2$ and $X_2$ form the second bond of a double bond at the 1,6 or 2,3 positions with the proviso that at least one of the groupings $R_1Z_1X_1R_2Z_2X_2$ and $R_1X_1Z_2$ form a hydroxamate moiety
(—N(OH)C(=O)—) in which $R_1$ and/or $R_2$ is N, $Z_1$ and/or $Z_2$ is =O and $X_1$ and/or $X_2$ is OH or $R_1$ is N, $Z_2$ is O and $X_1$ is OH and B is a 5 or 6 membered ring of formula II or III

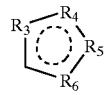

II

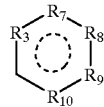

III in which $R_4$, $R_5$, $R_6$, $R_7$, $R_8$, $R_9$ and $R_{10}$ which may be the same or different are CH or N with the proviso that ring B cannot contain more than 3 ring members which are nitrogen and the ring B may optionally be substituted by one or more of hydroxy, keto (═O), or an optionally substituted alkyl, alkenyl, alkynyl, cycloalkyl, aryl or heterocyclyl group with the proviso that the compound is not

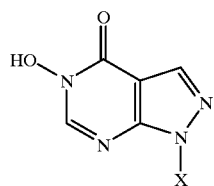

wherein X is hydrogen, aryl $C_{1-4}$ alkyl, or $C_{1-4}$ hydroxyalkyl or

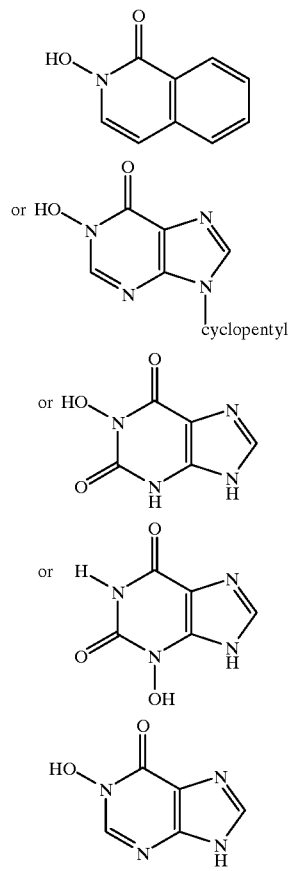

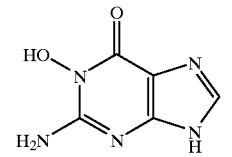

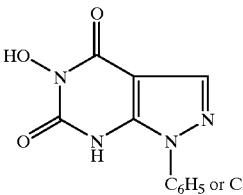

$C_6H_5$ or $CH_3$ or any compound of Formula I wherein ring B is substituted by a natural or unnatural sugar molecule or a salt thereof formed with a physiologically acceptable organic or inorganic acid for use in therapy.

According to a further aspect of the invention there is provided a pharmaceutical composition comprising a compound of formula I

I

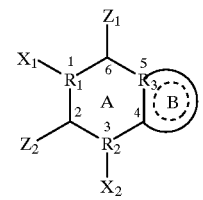

in which $R_1$, $R_2$ and $R_3$ which may be the same or different are N or CH, $X_1$ and $X_2$ which may be the same or different are hydrogen, hydroxy, or an optionally substituted alkyl, alkenyl, alkynyl, cycloalkyl, aryl or heterocyclyl group and $Z_1$ and $Z_2$ which may be the same or different are hydrogen, hydroxy, keto (═O) or an optionally substituted alkyl, alkenyl, alkynyl, cycloalkyl, aryl or heterocyclyl group or one of $Z_1$ and $X_1$ and $Z_2$ and $X_2$ form the second bond of a double bond at the 1,6 or 2,3 positions with the proviso that at least one of the groupings $R_1Z_1X_1$, $R_2Z_2X_2$ and $R_1X_1Z_2$ form a hydroxamate moiety (—N(OH)C(═O)—) in which $R_1$ and/or $R_2$ is N, $Z_1$ and/or $Z_2$ is ═O and $X_1$ and/or $X_2$ is OH or $R_1$ is N, $Z_2$ is ═O and $X_1$ is OH and B is a 5 or 6 membered ring of formula II or III

II

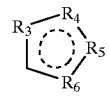

III

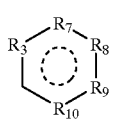

in which $R_4$, $R_5$, $R_6$, $R_7$, $R_8$, $R_9$ and $R_{10}$ which may be the same or different are CH or N with the proviso that B cannot contain more than 3 ring members which are nitrogen and the ring B may optionally be substituted by one or more of hydroxy, keto (═O) and an optionally substituted alkyl, alkenyl, alkynyl, cycloalkyl, aryl or heterocyclyl group with the proviso that the compound is not

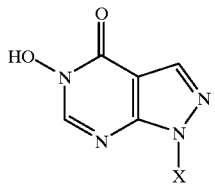

wherein X is hydrogen, aryl C$_{1-4}$ alkyl, or C$_{1-4}$ hydroxyalkyl

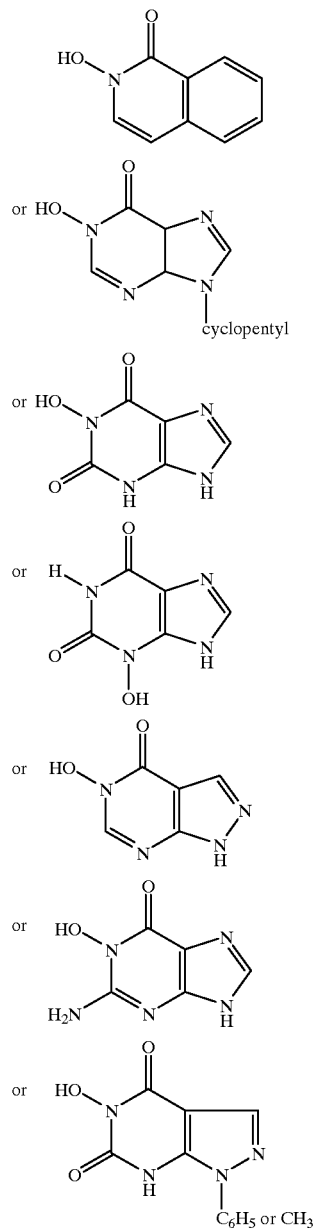

or a salt thereof formed with a physiologically acceptable organic or inorganic acid together with a psyiologically acceptable diluent or carrier. In general, compositions containing the compounds or formula II which are of particular interest are those in which the diluent or carrier excludes any liquid which is not sterile and pyrogen free.

As indicated the compounds of formula I may be formulated as salts formed with physiologically acceptable inorganic or organic acids. These salts may be prepared by conventional methods and it is preferred to use methane sulphonic acid, isethionic acid, lactic acid, tartaric acid or another solubilising acid.

The pharmaceutical composition of the invention may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients, using standard techniques well known to those skilled in the art of pharmacy.

It will be appreciated that the dosage levels used may vary over quite a wide range depending upon the compound used and the severity of the ischoemic condition of the patient and the patient's body weight. However, without commitment to a rigid definition of dosages it may be stated that a daily dosage of the active constituent (estimated as the free base) is 50–1000 mg. More particularly, the daily dosage for a 70 kg human administered parenterally will often be in the range from about 100 mg to about 500 mg, but with the more active compounds it may be less than this (the dose being varied pro-rata for humans of different weight or other mammals).

Where appropriate, the substances may also be compounded for oral administration in dosages which may be similar but may often be somewhat higher, so that the daily dose for a 70 kg human may often be in a range from 100–500 mg but may be somewhat less than this for the more active compounds. Such oral formulations may particularly take the form of tablets compounded in the presence of conventional solid carrier materials such as starch, lactose, dextrin and magnesium stearate, or of capsules or cachets. Suppositories, pessaries. aerosol and other formulations may also be employed. The compounds may be formulated in unit dosage form, i.e. in discrete portions each containing a unit dose, or a multiple or sub-multiple of a unit dose of the active ingredient.

The compounds of formula I described above find particular use for a wide range of ischaemic conditions where tissue has undergone damage caused by free radicals. Preferably however they find particular use for the treatment of reperfusion of the heart injury following myocardial infarction of the brain following a stroke.

BRIEF DESCRIPTION OF DRAWINGS

The invention is illustrated by the following Examples in which reference is made to the following Figures.

EXAMPLE 1

SYNTHESIS OF COMPOUNDS IN WHICH RING B IS PYRAZOLE

Figure 1A:
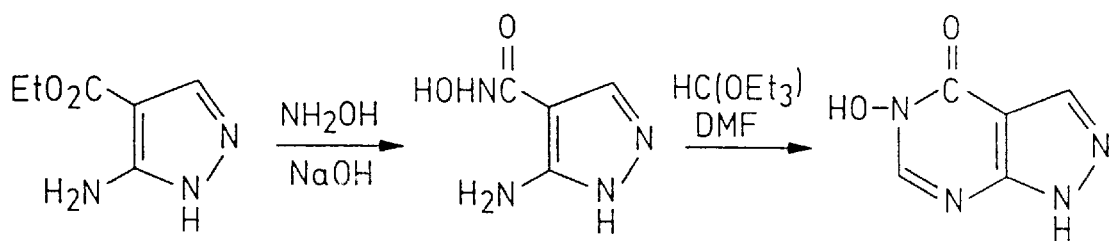
FIGS. 1a–c: shows schematic methods of preparation of compounds of Formula I wherein ring B is pyrazole.
Figure 1B:
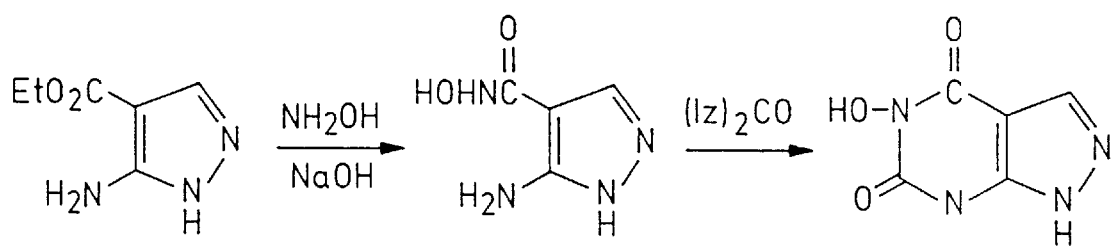
Figure 1C:
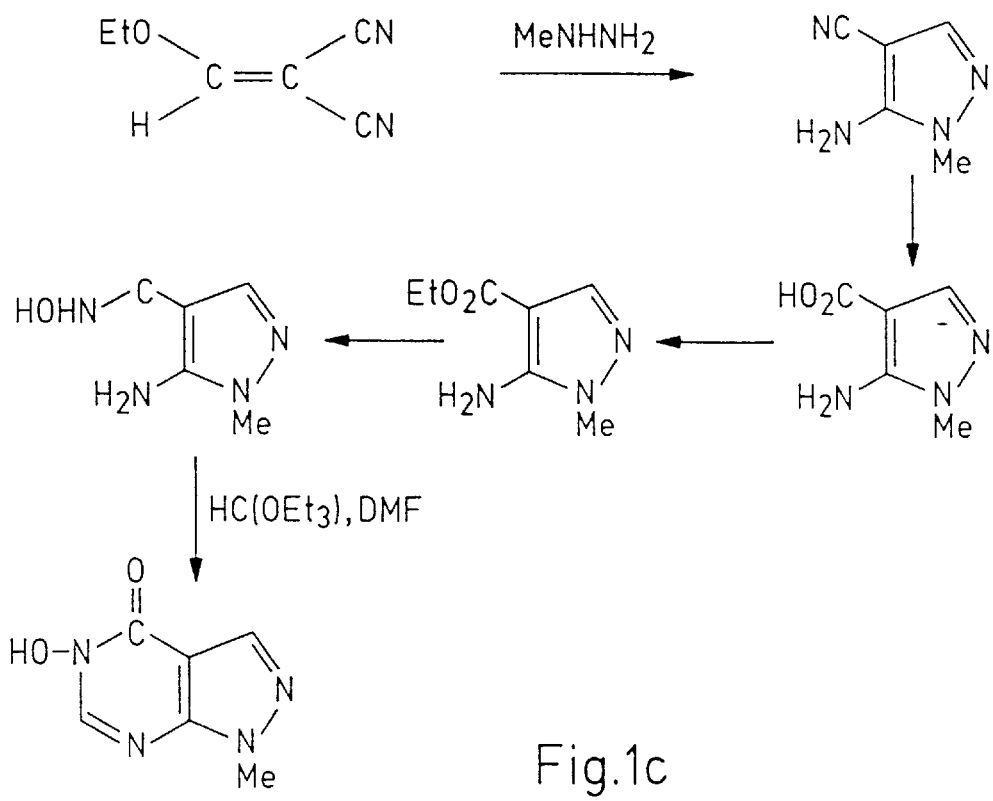

These syntheses are shown schematically in FIG. 1.

a) Synthesis of 1, hydroxy-6-oxypyrazolo-[3,4-d]-pyrimidine in the above general formula I, $R_1$ and $R_2$ are N, $R_3$ is CH, $X_1$ is OH, $Z_1$ is =O, $X_2$ and $Z_2$ form a double bond, ring B is of formula II in which $R_5$ and $R_6$ are N and $R_4$ is CH.

(i) To a solution of hydroxylamine hydrochloride (9.82 mmol) and sodium hydroxide (24 mmol) in water, was added 3-amino-4-carbethoxy pyrazole (6.44 mmol).

(ii) On completion of addition, the reaction mixture was stirred for 2 h at room temperature and then left to stand for 3 days.

(iii) The mixture was then acidified with dilute HCl and refrigerated until precipitation occurred.

(iv) The resultant hydroxamate was filtered, washed with ice-cold water and dried.

(v) The hydroxamate (6.28 mmol), triethylorthoformate (37.5 mmol) and DMF (175 mmol) were heated with stirring at –100° C. for 10–15 mins, or until precipitation occurred.

(vi) The reaction mixture was allowed to stand at room temperature for 18 h.

(vii) The product was then filtered and recrystallized from water.

Synthesis of 2,6-dioxo-1-hydroxypyrazolo-[3,4-d]-pyrimidine

Formula I is as described in (a) above except that $Z_2$ is keto (=O) and $X_2$ is H.

(i) 1.41 mmol of the hydroxamate (prepared as described above in (a)) in dry DMF (25.83 mmol) was added to a solution of 1,1-carbonyldiimidazole (1.425 mmol) in dry DMF (25.83 mmol).

(ii) The reaction mixture was then stirred at –100° C., under $N_2$, for 2 h or until reaction was complete.

(iii) The solvent was removed in vacuo and the resultant product recrystallized from water.

(c) Synthesis of 1-hydroxy-6-oxypyrazolo-[3,4-d]-9-methyl pyrimidine

Formula I is as described in (a) above except that the N is position $R_6$ is substituted with a methyl group.

(i) A mixture of ethoxymethylenemalonitrile (43.4 mmol) and methyl hydrazine (45.6 mmol) in ethanol was refluxed for 17 h.

(ii) The resulting 1-methyl-4-cyano-5-amino pyrazole precipitated out and was filtered and dried.

(iii) The 1-methyl-4-cyano-5-amino pyrazole was dissolved in 40% NaOH and the resulting solution refluxed for four days.

(iv) The solution was acidified with dilute HCl.

(v) The solvent was then removed in vacuo and the resulting acid recrystallised from ethanol.

(vi) The acid was converted to 1-methyl-4-carbethoxy-5-amino pyrazole using $SOCl_2$ and EtOH.

(vii) Proceed as in 1(a) steps i–viii.

EXAMPLE 2

SYNTHESIS OF COMPOUNDS IN WHICH RING B IS IMIDAZOLE

Figure 2:
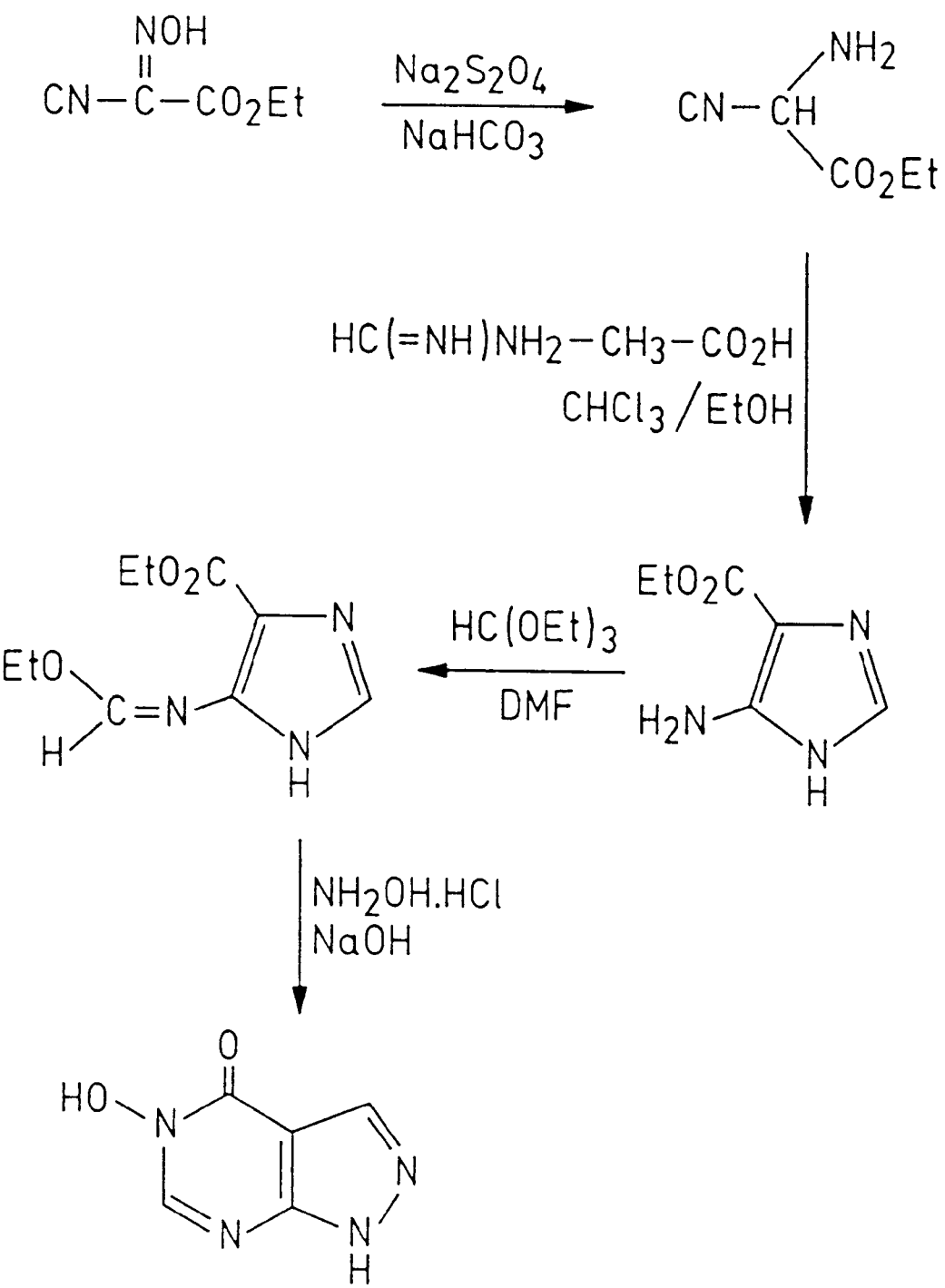
FIGS. 2 and 3: show schematic methods of preparation of compounds of Formula I wherein ring B is imidazole.
Figure 3:
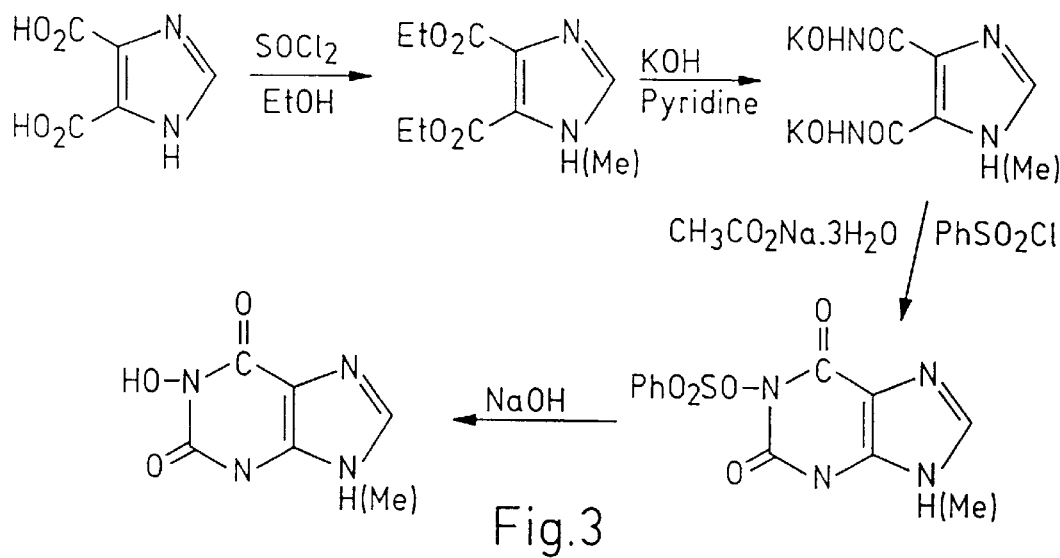

These syntheses are shown schematically in FIGS. 2 and 3.

(a) Synthesis of 1-hydroxy-6-oxopurine.

In formula I above, $R_1$ and $R_2$ are N, $R_3$ is CH, X is OH, $Z_1$ is keto, $Z_2$ and $X_2$ form a double bond, ring B is of formula II wherein $R_4$ and $R_6$ are N and $R_5$ is CH.

(i) To a solution of oxime (10 g) in water (60 ml) and saturated sodium bicarbonate (30 ml) was added sodium dithionite (34 g).

(ii) After 30 mins, the mixture was extracted with chloroform (×4) and dried ($Na_2SO_4$).

(iii) The solvent was removed in vacuo to give the 2-amino-2-cyanoacetate as an oil which was used immediately.

(iv) To a solution of the cyanoacetate (4 g), chloroform (80 ml), and ethanol (60 ml), was added formamidine acetate (4 g).

(v) The mixture was refluxed under $N_2$ for 2 h, after which it was evaporated to dryness.

(vi) The residue was taken up in chloroform (115 ml) and extracted with water (40 ml). The aqueous fraction was extracted with chloroform (3×20 ml) and the combined organic extracts were dried ($Na_2SO_4$), filtered, and evaporated to dryness.

(vii) The 4-amino-5-carbethoxy imidazole crystallized from ethyl acetate.

(viii) A solution of the imidazole (8.16 mmol) in triethylorthoformate (15 ml) and DMF (30 ml) was refluxed for 4 h.

(ix) The solvent was removed in vacuo and the resulting ethyl-forminidate-5-carbethoxyimidazole was recrystallized from ethanol.

(x) Cyclization to the corresponding hydroxamate was achieved as previously described.

(b) Synthesis of 3,8,9-trihydro-1-hydroxy-2,6dioxopurine

Formula I is the same as in (a) above except that $Z_2$ is keto (=O) and the $R_6N$ atom may be substituted by methyl.

(i) 4,5-imidazoledicarboxylic acid (46.76 mmol) was suspended in ethanol (330 ml) and cooled to –5° C.

(ii) $SOCl_2$ (95 ml) was added dropwise.

(iii) The reaction mixture was refluxed for 5 h and then allowed to cool.

(iv) On addition of dry diethyl ether turbidity occurred and the mixture was refrigerated until precipitation was complete.

(v) Resulting diethyl 4,5-imidazoledicarboxylate was then filtered and dried.

(vi) A solution of the dicarboxylate (15.11 mmol) and sodium ethoxide (19.71 mmol) in ethanol (160 ml) was treated with methyl iodide (22.67 mmol).

(vii) The reaction mixture was then refluxed for 4 h, after which the solvent was removed in vacuo and the residue treated with 5% $Na_2CO_3$.

(viii) The product was extracted into chloroform, dried ($Na_2SO_4$), and filtered.

(ix) Removal of the solvent in vacuo and subsequent distillation furnished diethyl 1-methyl-4,5-imidazoledicarboxylate (b.p –148–150° C., 0.25 mmHg).

(x) To a suspension of KOH (56.28 mmol) in pyridine (25 ml) was added an ice-cold solution of hydroxylamine hydrochloride (32.78 mmol) in pyridine (25 ml).

(xi) The dicarboxylate (14.07 mmol) was added and stirring continued for 2.5 h at 0–5° C.

(xii) Stirring was then continued at room temperature for 18 h, after which the resulting solids were filtered and dried.

(xiii) The salt formed (15.55 mmol) was suspended in THF (25 ml) and a solution of benzenesulfonyl chloride (13.06 mmol) in THF (7 ml) was added as such a rate as to maintain the temperature at 20–22° C.

(xiv) Stirring was continued for 30 min and sodium acetate trihydrate (6.13 mmol) added.

(xv) The reaction mixture was then stirred for 2 h and the solids were filtered, and washed with THF (3×10 ml).

(xvi) The THF was removed in vacuo and the residue partitioned between water (30 ml) and petroleum ether (16 ml).

(xvii) The resulting precipitate, the 1-benzenesulfonyloxy-7-methylxanthine, was collected and recrystallized from ethanol.
(xix) The above compound was dissolved in sodium hydroxide solution, which was the then refluxed until it became clear.
(xx) The solution was cooled, and acidified with conc. HCl.
(xxi) The reaction mixture was kept in an ice-bath until precipitation occurred, and the resulting 1-hydroxy-7-methylxanthine was recrystallized from water.

EXAMPLE 3

SYNTHESIS OF COMPOUNDS IN WHICH RING B IS PYRAZINE

Figure 4A:
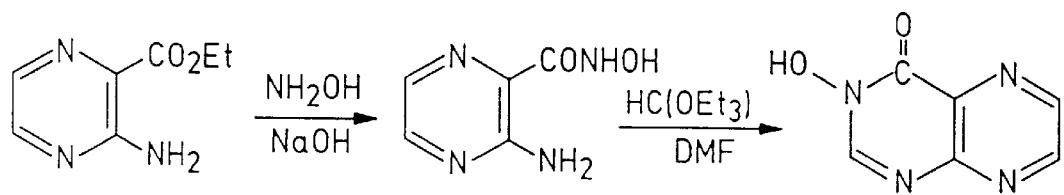
FIGS. 4a, b: shows schematic methods of preparation of compounds of Formula I wherein ring B is pyrazine.
Figure 4B:
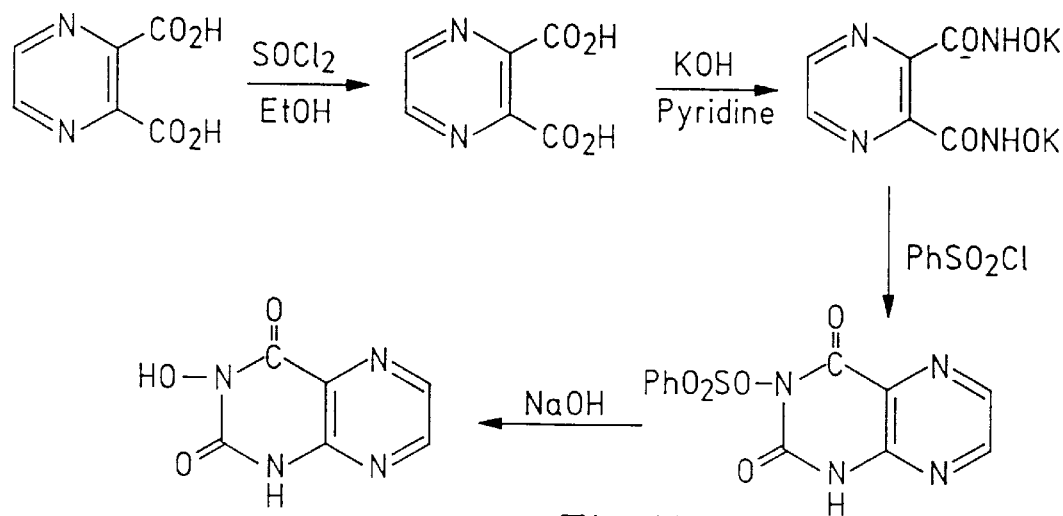

These syntheses are shown schematically in FIG. 4.
a) Synthesis of 1-hydroxy-6-oxypyrazino-[2,3-d]-pterine
In formula I, $R_1$ are $R_2$ and N, $R_3$ is CH, $X_1$ is OH, $Z_1$ is keto, $Z_2$ and $X_2$ form a double bond, ring B is of formula III wherein $R_7$ and $R_{10}$ are N and $R_8$ and $R_9$ are CH.
(i) 3-aminopyrazine-2-carboxylic acid (14.37 mmol) was suspended in ethanol (50 ml) and cooled to −5° C.
(ii) $SOCl_2$ (20 mmol) was added dropwise.
(iii) The reaction mixture was refluxed for 5 h and then filtered hot.
(iv) On cooling precipitation occurred to give ethyl 3-aminopyrazine-2-carboxylate.
(v) The ester was then treated with NaOH and $NH_2OH.HCl$ as previously described to give the hydroxamate which was subsequently cyclized using triethylorthoformate and DMF; the mixture being stirred at −160°.
(b) Synthesis of 2,6-dioxo-1-hydroxypyrazino-[2,3-d] pteridine
Formula I is as described above except $Z_2$ is keto and $X_2$ is H.
The diketo-pterine compound was prepared using the procedure described for 1-hydroxy-7-methylxanthine in Example 1(c) above.

EXAMPLE 4

SYNTHESIS OF COMPOUNDS IN WHICH RING B IS TRIAZOLE

Figure 5:
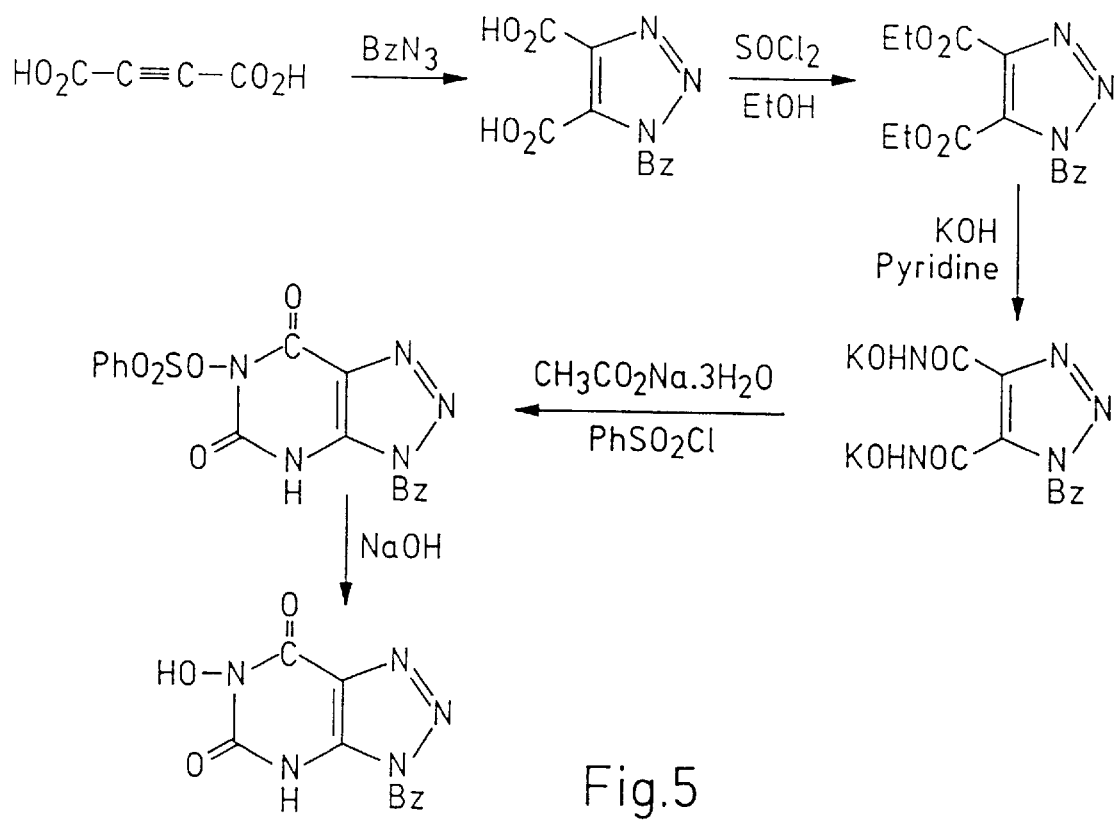
FIG. 5: shows schematic methods of preparation of compounds of Formula I wherein ring B is triazole.

This synthesis is shown schematically in FIG. 5.
(a) Synthesis of 9-benzyl-2,6-dioxo-1-hydroxytriazalo-[3,4-d] azapurine
In formula I, $R_1$ and $R_2$ are N, $R_3$ is CH, $Z_1$ is keto, $X_1$ is OH, $Z_2$ is keto, $X_2$ is H, ring B is of formula II in which $R_4$, $R_5$, and $R_6$ are N and $R_6$ is substituted by benzyl.
(i) Benzyl chloride (158 mmol) was added to a suspension of sodium azide (230 mmol) in ethanol (45 ml).
(ii) The reaction mixture was refluxed for 6 h and then allowed to cool.
(iii) On the addition of water, the benzyl azide separated out as an oil which was distilled (−200°/760 mmHg) and dried over $CaCl_2$.
(iv) To a solution of acetylenedicarboxylic acid (25.7 mmol) in acetone (10 ml) was added benzyl azide (35.6 mmol).
(v) The solution heated up rapidly to reflux and external cooling was required.
(vi) The product began to crystallize almost immediately, and after being allowed to stand over night was filtered.
(vii) The remainder of the procedure is as described for 1-hydroxy-7-methylxanthine.

EXAMPLE 5

SYNTHESIS OF COMPOUNDS IN WHICH RING B IS PYRIDINE

Figure 6:
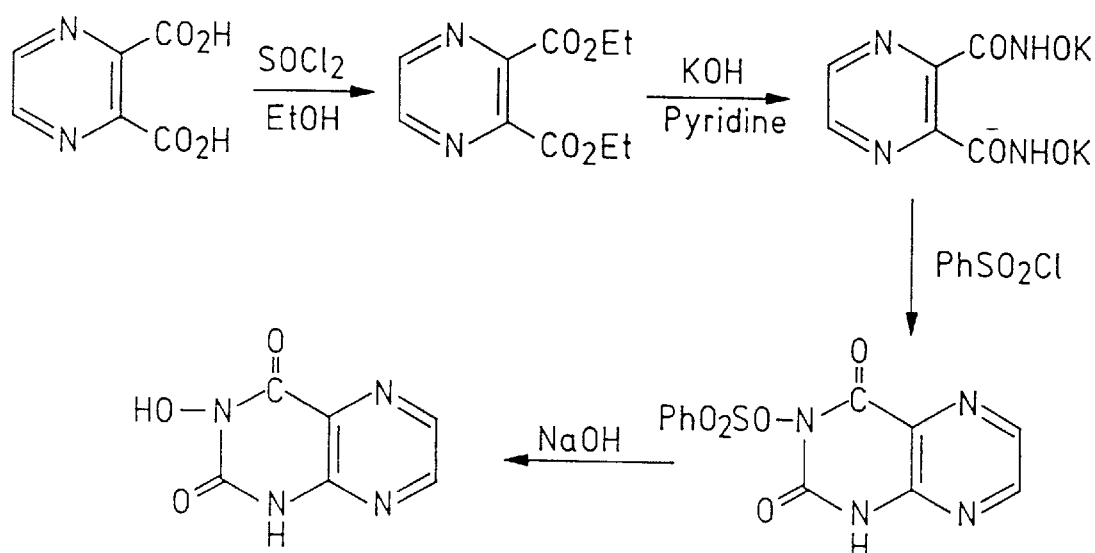
FIG. 6: shows schematic methods of preparation of compounds of Formula I wherein ring B is pyridine.

This synthesis is shown schematically in FIG. 6.
(a) Synthesis of 2,6-dioxo-1-hydroxypyrido-[2,3-d] pyrimidine
In formula I, $R_1$ and $R_2$ are N, $R_3$ is CH, $Z_1$ and $Z_2$ are keto, $X_1$ is OH, $X_2$ is H, ring B is of formula III in which $R_{10}$ is N, $R_7$, $R_8$, are CH.
(i) The procedure is as described for 1-hydroxy-7-methylxanthine in example 1(c) above.

EXAMPLE 6

List of specific Compounds

In this and the following examples, the following compounds are referred to by reference number.

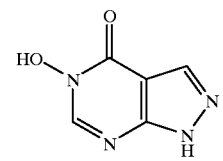

SL 100

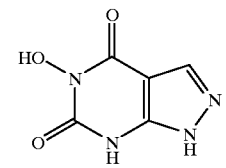

SL 101

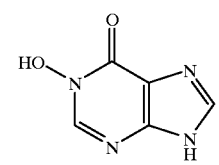

SL 200

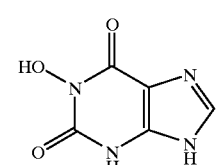

SL 201

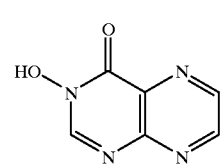

SL 300

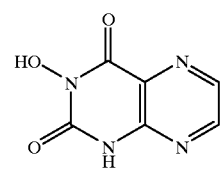

SL 301

XANTHINE OXIDASE INHIBITION ASSAY

Superoxide produced from the oxidation of varying concentrations of xanthine to uric acid in the presence of xanthine oxidase (5×10$^{-3}$ U/ml) was quantified by the superoxide dismutase inhibitable reduction of cytochrome c oxidase (10 μM) at 550 nm with respect to time. Enzyme inhibition was determined at varying concentrations of the inhibitors. Results obtained are expressed as percentage inhibition of initial rate of reaction in comparison to controls and are shown in Table 1–4 below.

TABLE 1

[Xanthine] = 50 μM

| | % Inhibition % S.D. Inhibitor Conc. (μM) | | | |
|---|---|---|---|---|
| | 1 μM | 5 μM | 10 μM | 50 μM |
| Allopurinol | 13.83% 3.21 | 22.90% 3.21 | 20.63% 6.41 | 59.18% 11.11 |
| Oxypurinol | 2.26% 0.91 | 24.81% 2.21 | 32.33% 10.64 | 67.42% 9.38 |
| SL300 | N.A.* | 1.84% 2.60 | 14.17% 5.02 | 16.01% 3.71 |
| SL301 | 29.13% 2.21 | 31.75% 3.71 | 39.63% 3.72 | 63.25% 3.71 |

*N.A. - not acitve.

Values are expressed as percentage inhibition of the initial rate of reaction with respect to control % standard deviation, n=3.

TABLE 2

[Xanthine] = 25 μM

| | % Inhibition % S.D. Inhibitor Conc. (μM) | | | |
|---|---|---|---|---|
| | 1 μM | 5 μM | 10 μM | 50 μM |
| Allopurinol | N.A.* | 2.41% 3.40 | 14.09% 4.86 | 58.76% 8.42 |
| Oxypurinol | 2.26% 0.92 | 37.34% 9.38 | 42.36% 12.78 | 62.40% 16.24 |
| SL300 | 13.75% 3.30 | 9.09% 1.02 | 16.08% 3.1 | 34.73% 3.30 |
| SL301 | 37.06% 3.31 | 51.05% 2.76 | 58.04% 4.21 | 72.03% 2.51 |

*N.A. - not active.

Values are expressed as percentage inhibition of the initial rate of reaction with respect to control % standard deviation, n=3.

TABLE 3

[Xanthine] = 25 μM

| | % Inhibition % S.D. Inhibitor Conc. (μM) | | | |
|---|---|---|---|---|
| | 1 μM | 5 μM | 10 μM | 50 μM |
| Allopurinol | 23.88% 9.82 | 64.57% 3.94 | 44.88% 6.34 | 68.50% 23.18 |
| Oxypurinol | 15.38% 3.21 | 46.15% 6.28 | 30.77% 12.56 | 43.59% 3.63 |
| SL300 | N.A.* | 5.55% 3.93 | 11.11% 7.86 | 27.78% 7.85 |
| SL301 | 25.00% 3.21 | 41.67% 2.52 | 58.33% 2.67 | 77.78% 3.93 |

*N.A. - not active.

Values are expressed as percentage inhibition of the initial rate of reaction with respect to control % standard deviation, n=3.

TABLE 4

[Xanthine] = 8 μM

| | % Inhibition % S.D. Inhibitor Conc. (μM) | | | |
|---|---|---|---|---|
| | 1 μM | 5 μM | 10 μM | 50 μM |
| Allopurinol | 17.40% 4.17 | 29.20% 3.71 | 49.85% 11.04 | 73.45% 7.23 |
| Oxypurinol | 6.06% 4.29 | 33.33% 4.29 | 45.45% 7.42 | 48.48% 8.57 |
| SL300 | 6.15% 4.58 | 12.62% 3.12 | 19.09% 4.58 | 38.51% 12.11 |
| SL301 | 22.33% 4.51 | 41.75% 11.42 | 49.75% 9.13 | 70.87% 6.78 |

SL100, SL101, SL200, SL201 were found to be inactive.

Values are expressed as percentage inhibition of the initial rate of reaction with respect to control % standard deviation, n=3.

FURTHER XANTHINE OXIDASE INHIBITION STUDIES

The inhibition of xanthine oxidase by allopurinol and SL301 was studied by steady-state kinetic analysis. The study was conducted at 37° C. using 30 mU/ml bovine xanthine oxidase in 50 mM phosphate buffer (ph 7.4). The initial rate of uric acid formation was determined spectrophotometrically (292 nm) in the presence of varying concentrations of xanthine (5, 7.5, 10, 15 and 20 μM) and the inhibitors (1–3 μM). Enzyme-inhibitor dissociation constant ($K_i$) values were calculated from the apparent $1/V_{max}$ values obtained at different inhibitor concentrations.

The average $K_i$ values obtained for allopurinol and SL301 were 2.4 and 0.7 μM respectively. both compounds were found to inhibit xanthine oxidase in a competitive manner.

EXAMPLE 7

HYDROXYL RADICAL SCAVENGING ACTIVITY

Antioxidant activity is based on the selective hydroxylation of NPG (N,N'-[5-nitro-1,3-phenylene] bisglutaramide) by hydroxyl radicals produced from peroxynitrous acid (1 mM) by the addition of peroxynitrite stabilised in base to a mixture of NPG (1 mM) and varying concentrations of the anti-ischaemic agents prepared in 0.2M phosphate buffer, pH 7. The solutions were analysed by RP-HPLC. NPS (50 mM), an analogue of NPG, was used as an internal standard. Inhibition of hydroxylation of NPG is a direct measure of the hydroxyl radical scavenging ability of the inhibitors. Results are expressed as the percentage scavenging of the hydroxyl radical compared to controls and are shown in Table 5 below.

TABLE 5

| | % Activity % S.D. Antioxidant Ratio | | | |
|---|---|---|---|---|
| | 0.1 | 0.5 | 1.0 | 5.0 |
| SL100 | 6.56% 7.08 | 37.70% 6.69 | 65.58% 5.35 | 100 |
| SL101 | 8.25% 5.35 | 20.96% 5.44 | 39.71% 11.0 | 72.79% 0.26 |
| SL200 | 25.13% 5.01 | 48.49% 5.45 | 69.54% 0.50 | 90.09% 0.15 |
| SL300 | N.A. | 6.04% 3.20 | 26.58% 4.74 | 68.58% 3.50 |
| SL301 | 9.80% 8.03 | 18.00% 5.35 | 45.90% 4.02 | 70.21% 0.46 |

*N.A. - not active.

Values are expressed as percentage scavenging of the hydroxyl radicals % standard deviation, n=3.

EXAMPLE 8

HEART ISCHAEMIA REPERFUSION STUDIES

Adult male Wistar rats (240–320 g) were anaesthetised intraperitoneally (i.p.) with sodium pentobarbital (Sagatal; 60 mg/kg and heparinised (100 IU/100 g body weight) through the femoral vein, and the heart excised in cold Krebs buffer. By Langendorff technique, the hearts were perfused at a constant pressure (100 mm $H_2O$) with Krebs bicarbonate buffer. The study was initiated by 30 min aerobic perfusion followed by a 50 min period of global ischaemia, achieved by clamping perfusion flow into the aorta, and finally by reperfusion over 60 min. A ballon was inserted into the left ventricle and inflated to a left ventricular end diastolic pressure (LVEDP) of 4 mm Hg and used to measure left ventricular developed pressure (LVDP) and heart rate (HR). In addition, the coronary effluent was collected over timed intervals as a measure of coronary flow (CF). Assessment of function was made 20 min after the start of the study and at 10 min intervals thereafter. SL301 treated hearts followed a similar protocol as above except that the drug was present in the reperfusion perfusate following the ischaemic insult.

The results are shown in Table 6 below.

TABLE 6

% recovery (±sem) of pre-ischaemic function after 60 min. of aerobic perfusion following ischaemia (50 min.) in control and SL301 (150 μM) perfused rat hearts

|      | CONTROL | SL301   |
|------|---------|---------|
| LVDP | 41 ± 13 | 76 ± 9* |
| HR   | 49 ± 13 | 90 ± 6* |
| CF   | 83 ± 6  | 72 ± 4  |

We claim:

1. A pharmaceutical composition comprising a pharmaceutically acceptable diluent or carrier and a compound of formula I

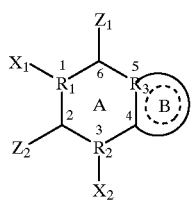

in which $R_1$ and $R_2$ are N;

$X_1$ and $X_2$ are independently selected from the group consisting of hydrogen, hydroxy, and an optionally substituted alkyl group; and $Z_1$ and $Z_2$ are independently selected from the group consisting of hydrogen, hydroxy, and keto (=O); or one of the pair $Z_1$ and $X_1$ and the pair $Z_2$ and $X_2$ form a second bond of a double bond at the 1,6 or 2,3 positions; and B is a 5 or 6 membered ring selected from the group represented by formula II and III

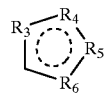

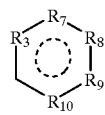

in which in formula II $R_4$ and $R_6$ are N and $R_3$ and $R_5$ are CH or $R_5$ and $R_6$ are N and $R_3$ and $R_4$ are CH, and in formula III $R_7$ and $R_{10}$ are N and $R_3$, $R_8$ and $R_9$ are CH; with the proviso that firstly at least one of the groupings selected from $R_1X_1C(6)Z_1$, $R_2X_2C(2)Z_2$ and $R_1X_1C(2)Z_2$, in which C(2) and C(6) represent the 2- and 6-positions respectively of the ring A, form a hydroxamate moiety (—N(OH)C(=O)—); and secondly that the compound is not

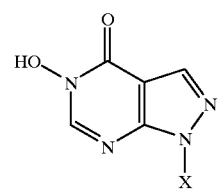

wherein X is hydrogen, aryl $C_{1-4}$ alkyl, or $C_{1-4}$ hydroxyalkyl or

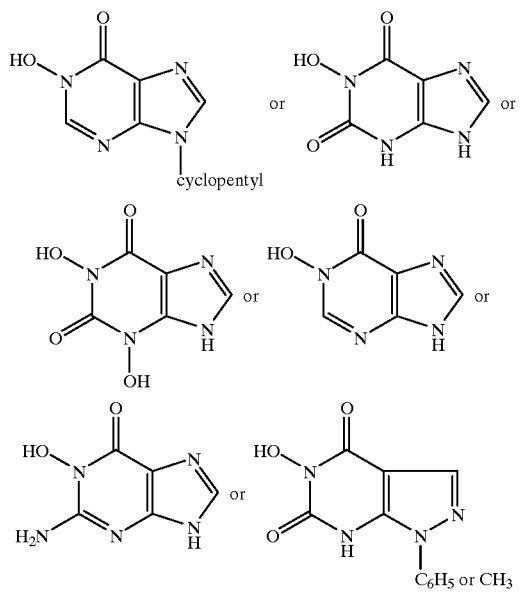

or a salt thereof formed with a pharmaceutically acceptable organic or inorganic acid.

2. A pharmaceutical composition according to claim 1 in which the ring B is substituted by one or more groups selected from hydroxy, keto (=O), an optionally substituted alkyl, an optionally substituted alkenyl, an optionally substituted alkynyl, an optionally substituted cycloalkyl, an optionally substituted aryl and an optionally substituted heterocyclyl group.

3. A pharmaceutical composition according to claim 1 in which ring A contains one hydroxamate moiety.

4. A pharmaceutical composition according to claim 1 in which the hydroxamate moiety is at position 2,3 of ring A.

5. A pharmaceutical composition according to claim 1 in which ring A includes a keto group at positions 2 and 6 respectively.

6. A pharmaceutical composition according to claim 4 in which ring B is unsubstituted.

7. A pharmaceutical composition according to claim 4 in which the ring B is a 6-membered ring of Formula III

III

8. A pharmaceutical composition according to claim 1 in which the compound of formula (I) is 9. A pharmaceutical composition according to claim 1 in the form of a unit dosage form.

10. A pharmaceutical composition according to claim 1 in the form of a tablet, a capsule, aqueous or oily solution, suspension or emulsion.

11. A method of preventing or treating ischaemia comprising the administration to a patient requiring therapy of a pharmaceutically acceptable amount of a compound of formula I

I or a salt thereof formed with a pharmaceutically acceptable organic or inorganic acid in which $R_1$ and $R_2$ are N;

$X_1$ and $X_2$ are independently selected from the group consisting of hydrogen, hydroxy, and an optionally substituted alkyl; and $Z_1$ and $Z_2$ are independently selected from the group consisting of hydrogen, hydroxy, and keto (=O); or one of the pair $Z_1$ and $X_1$ and the pair $Z_2$ and $X_2$ form a second bond of a double bond at the 1,6 or 2,3 positions; and B is a 5 or 6 membered ring selected from the group represented by formula II and III

II

III in which in formula II $R_4$ and $R_6$ are N and $R_3$ and $R_5$ are CH or $R_5$ and $R_6$ are N and $R_3$ and $R_4$ are CH, and in formula III $R_7$ and $R_{10}$ are N and $R_3$, $R_8$ and $R_9$ are CH; with the proviso that at least one of the groupings selected from $R_1X_1C(6)Z_1$, $R_2X_2C(2)Z_2$ and $R_1X_1C(2)Z_2$, in which C(2) and C(6) represent the 2- and 6-positions respectively of the ring A, form a hydroxamate moiety (—N(OH)C(=O)—).

12. A method according to claim 11 in which the ring B is substituted by one or more groups selected from hydroxy, keto (=O), an optionally substituted alkyl, an optionally substituted alkenyl, an optionally substituted alkynyl, an optionally substituted cycloalkyl, an optionally substituted aryl and an optionally substituted heterocyclyl group.

13. A method according to claim 11 in which ring A contains one hydroxamate moiety.

14. A method according to claim 11 in which the hydroxamate moiety is at position 2,3 of ring A.

15. A method according to claim 11 in which ring A includes a keto group at positions 2 and 6 respectively.

16. A method according to claim 11 in which ring B is unsubstituted.

17. A method according to claim 11 in which the ring B is a 6-membered ring of Formula III.

18. A method according to claim 11 in which the compound of formula (I) is

19. A method according to claim 11 in which the compound is administered in the form of a unit dosage form.

20. A method according to claim 11 in which the compound is administered in the form of a tablet, a capsule, aqueous or oily solution, suspension or emulsion.

* * * * *